(12) United States Patent
Matsumura et al.

(10) Patent No.: US 8,705,698 B2
(45) Date of Patent: Apr. 22, 2014

(54) X-RAY ANALYZER AND MAPPING METHOD FOR AN X-RAY ANALYSIS

(75) Inventors: Hiroshi Matsumura, Chiba (JP); Kiyoshi Hasegawa, Chiba (JP)

(73) Assignee: SII Nanotechnology Inc. (JP)

( * ) Notice: Subject to any disclaimer, the term of this patent is extended or adjusted under 35 U.S.C. 154(b) by 580 days.

(21) Appl. No.: 13/027,881

(22) Filed: Feb. 15, 2011

(65) Prior Publication Data
US 2011/0206186 A1 Aug. 25, 2011

(30) Foreign Application Priority Data

Feb. 19, 2010 (JP) ................................ 2010-035233

(51) Int. Cl.
*H05G 1/62* (2006.01)
*G01N 23/201* (2006.01)
*G06K 9/78* (2006.01)
*G06K 9/82* (2006.01)

(52) U.S. Cl.
USPC .............. 378/87; 378/88; 378/98.3; 382/130; 382/132

(58) Field of Classification Search
USPC ............. 378/6, 44, 45, 49, 62, 63, 70, 82, 86, 378/87, 88, 98, 98.2, 98.3, 98.7, 98.8, 98.9, 378/98.11, 98.12, 204, 210; 382/165, 254, 382/274, 276, 325, 128, 130–132, 145, 147, 382/149
See application file for complete search history.

(56) References Cited

U.S. PATENT DOCUMENTS

2010/0002833 A1\* 1/2010 Matoba et al. .................. 378/44
2010/0034353 A1\* 2/2010 Kravis et al. .................... 378/87

FOREIGN PATENT DOCUMENTS

| JP | 04-175647 A | 6/1992 |
| JP | 11-264805 A | 9/1999 |
| JP | 2006-119108 A | 5/2006 |
| JP | 2007-163183 A | 6/2007 |
| JP | 2009-300232 A | 12/2009 |

\* cited by examiner

*Primary Examiner* — Anastasia Midkiff
(74) *Attorney, Agent, or Firm* — Brinks Gilson & Lione

(57) ABSTRACT

Provided are an X-ray analyzer and a mapping method for an X-ray analysis which, in a inspection for a harmful substance contained in, for example, a material or a composite electronic component, enable determination as to whether a sample is normal or abnormal to be performed visually based on an image obtained by the X-ray mapping analysis. In the X-ray analyzer, an X-ray mapping image of a sample which is confirmed to be normal in advance is obtained as a reference mapping image. A mapping analysis is performed on a inspection sample. A difference from the reference mapping image is obtained for each pixel, to thereby display a difference mapping image. A region in which the amount of specific element is larger than a reference amount is displayed with high brightness, and hence an abnormal portion may be easily found.

15 Claims, 6 Drawing Sheets

F I G. 3 C
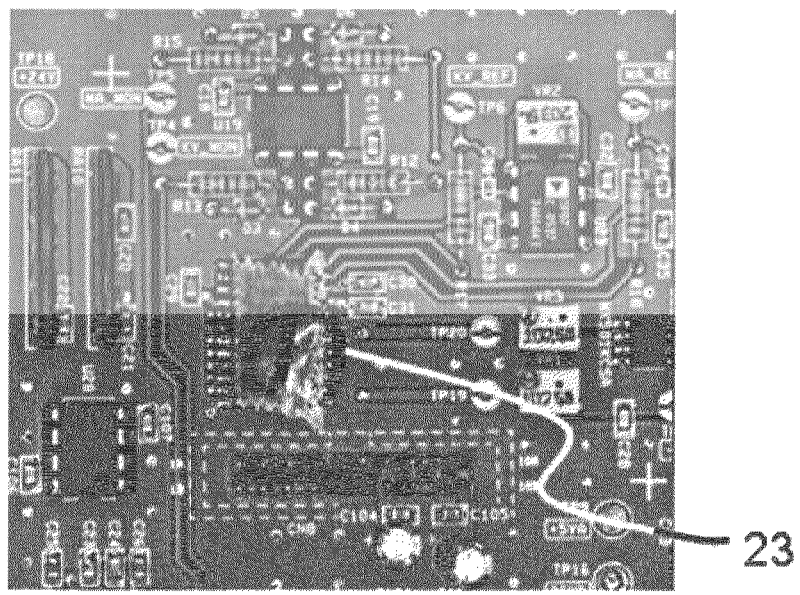

F I G . 4
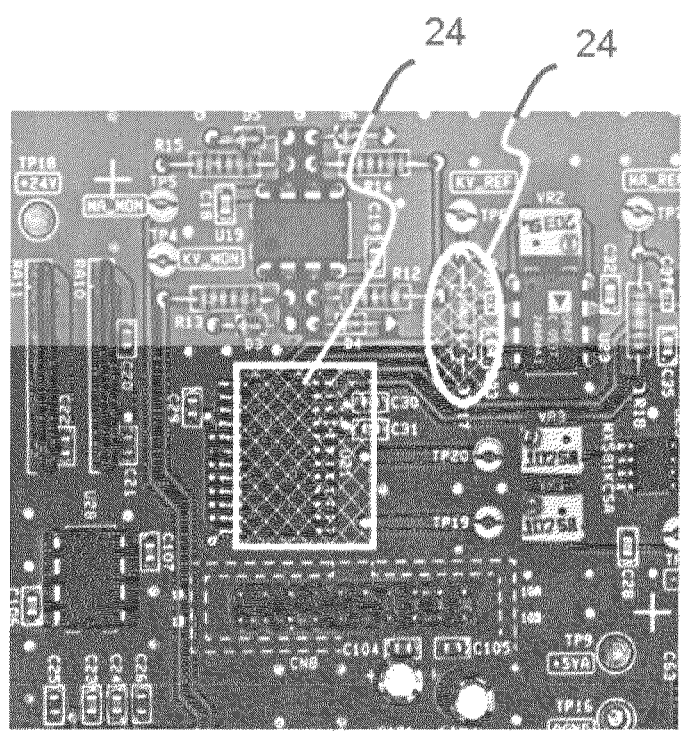

X-RAY ANALYZER AND MAPPING METHOD FOR AN X-RAY ANALYSIS

RELATED APPLICATIONS

This application claims priority under 35 U.S.C. §119 to Japanese Patent Application No. 2010-035233 filed on Feb. 19, 2010, the entire content of which is hereby incorporated by reference.

BACKGROUND OF THE INVENTION

1. Field of the Invention

The present invention relates to an X-ray analyzer and a mapping method which are suitable for performing an X-ray mapping analysis on a surface of a sample through, for example, a fluorescent X-ray analysis.

2. Description of the Related Art

A fluorescent X-ray analysis is used to perform a qualitative analysis or a quantitative analysis of a sample by irradiating the sample with an X-ray emitted from an X-ray source to detect, with an X-ray detector, a fluorescent X-ray which is a characteristic X-ray emitted from the sample, and by obtaining a spectrum from energy of the fluorescent X-ray. The fluorescent X-ray analysis enables the non-destructive and quick analysis of the sample, and therefore the fluorescent X-ray analysis is widely used in manufacturing process management, quality control, or the like. In recent years, precision and sensitivity have been increased in the X-ray analysis, which enables trace measurement. Accordingly, there is expected the diffusion of the fluorescent X-ray analysis as an analysis technique of performing detection especially of a harmful substance contained in a material, a composite electronic component, or the like (for example, Japanese Unexamined Patent Application Publication Nos. 2006-119108 and 2007-163183).

As analysis techniques in the fluorescent X-ray analysis, there are a wavelength dispersive method of splitting a fluorescent X-ray by an analyzing crystal to measure a wavelength and an intensity of the X-ray, an energy dispersive method of detecting a fluorescent X-ray with a semiconductor detector without splitting the fluorescent X-ray to measure an energy and an intensity of the X-ray with a pulse height analyzer, and the like.

Conventionally, for example, Japanese Unexamined Patent Application Publication Nos. 1992-175647, 1999-264805, and 2009-300232 propose an X-ray analyzer including an X-ray tube for irradiating a sample with an X-ray, an X-ray detector for detecting a fluorescent X-ray generated from the sample irradiated with the X-ray, a pulse processor for discriminating an element contained in the sample and its intensity based on an output of the X-ray detector, a computer to which a signal transmitted from the pulse processor is input, an image processing device for processing an output of the computer to display a distribution of an X-ray intensity in a two-dimensional image, and imaging means for imaging an optical observation image which corresponds to an image of the x-ray intensity.

An X-ray mapping analysis has been performed in order to detect a harmful substance contained in, for example, a material or a composite electronic component. Up to now, even when an X-ray intensity distribution of a focused element, for example, a harmful substance, is presented, a reference for defining a normal intensity region in the intensity distribution is not apparently specified and it is difficult to determine whether or not a detected position is really a position to be compared.

SUMMARY OF THE INVENTION

The present invention has been made in view of the problem described above. An object of the present invention is to provide an X-ray analyzer and a mapping method for an X-ray analysis which enable quick determination as to whether or not there is any abnormal region to be performed visually at an adequate position based on an image obtained by the X-ray mapping analysis.

In order to solve the above-mentioned problem, an X-ray analyzer according to the present invention includes: a radiation source for irradiating an irradiation point on an inspection sample with a radiation; an X-ray detector for detecting a characteristic X-ray and a scattered X-ray which are radiated from the inspection sample to output, as an X-ray intensity, a signal containing energy information on the characteristic X-ray and the scattered X-ray; an analyzer for analyzing the signal; a movable sample stage for shifting the irradiation point relative to the inspection sample within a mapping area set in advance; an optical microscope system for imaging the mapping area and displaying an image of the mapping area; and an X-ray mapping processing section for discriminating an X-ray intensity corresponding to at least one specific element from an analysis result obtained by the analyzer and determining an intensity contrast in which one of a color and lightness is changed in accordance with the X-ray intensity to perform image display at a position corresponding to the irradiation point in the mapping area, in which the X-ray mapping processing section includes: reference mapping image storing means for storing a reference mapping image in a measurement area, of a reference sample which is of the same type as the inspection sample and is normal; inspection mapping image storing means for storing an inspection mapping image of the inspection sample in an area corresponding to the inspection area; difference calculation means for calculating a difference between an X-ray intensity of the reference mapping image and an X-ray intensity of the inspection mapping image at a corresponding position for each pixel; and difference mapping image output means for outputting a difference mapping image generated based on the difference.

According to a feature of the X-ray analyzer of the present invention, a part of the difference mapping image in which the amount of a specific element is smaller than a normal amount is displayed with high brightness. Parts of the difference mapping image in which the amount of the specific element is larger than the normal amount and the amount of the specific element is smaller than the normal amount are displayed in different colors with high brightness levels corresponding to absolute values of differences. Therefore, changes of the inspection mapping image and the reference mapping image may be visually recognized.

According to a feature of the X-ray analyzer of the present invention, the inspection mapping image, the reference mapping image, and the difference mapping image corresponding to a difference between the two images are arranged and displayed to make the difference clear.

According to a feature of the X-ray analyzer of the present invention, when there are a plurality of focused elements, the inspection mapping images, the reference mapping images, and the difference mapping images for the respective elements are simultaneously arranged and displayed to improve inspection efficiency.

According to a feature of the X-ray analyzer of the present invention, the optical microscope image in the mapping area and the difference mapping image are superimposed on each other and displayed, and hence an abnormal region may be determined from the optical microscope image.

According to a feature of the present invention, when the inspection mapping image and the reference mapping image are to be obtained, the optical microscope images in the same area as the mapping area are obtained, and rotation correction, position correction, and scale correction are performed using the two optical microscope images. Therefore, the difference mapping image may be accurately obtained to improve inspection precision. Similarly, the two X-ray mapping images, namely, the inspection mapping image and the reference mapping image may be used to perform rotation correction, position correction, and scale correction.

According to a feature of the X-ray analyzer of the present invention, in the case where the reference mapping image is to be obtained, when an intensity difference of the contained element from the inspection sample is known, an area to be eliminated from the inspection area of the inspection sample in advance is specified on the mapping image and the optical microscope image, or an image in which the inspection elimination area is masked is produced as external image data and captured, to thereby obtain the difference mapping image only in an area required for an inspection.

Further, according to a feature of the X-ray analyzer of the present invention, image data captured from an outside is stored as the reference mapping image. Therefore, when the reference mapping image is distributed to a plurality of X-ray analyzer, the same reference mapping image may be used. Thus, normal and abnormal determinations are unified, and hence the same inspections may be simultaneously performed.

According to a feature of the mapping method for an X-ray analysis of the present invention, the reference mapping image and the inspection mapping image are obtained, and the difference between the X-ray intensities associated with the specific element at the relative positions is calculated to output the difference mapping image.

The present invention has the following effect.

That is, according to the X-ray analyzer and the mapping method for an X-ray analysis of the present invention, the difference between the reference mapping image as the reference and the mapping image of the inspection sample is displayed. Therefore, a problem region in which the amount of a specific element is equal to or larger than a reference amount may be visually determined with ease, and hence an inspection for a harmful substance may be performed accurately and efficiently.

BRIEF DESCRIPTION OF THE DRAWINGS

In the accompanying drawings:

FIG. 3C is a concept view illustrating a superimposed image of an optical microscope image and a difference mapping image in the present invention; and FIG. 4 is a concept view illustrating an inspection elimination area in the present invention.

DETAILED DESCRIPTION OF THE PREFERRED EMBODIMENT

Hereinafter, an X-ray analyzer according to an embodiment of the present invention is described with reference to FIGS. 1 to 4. In each of the drawings referred to in the following description, scale size is appropriately changed to illustrate each member in a recognizable manner.

Figure 2:
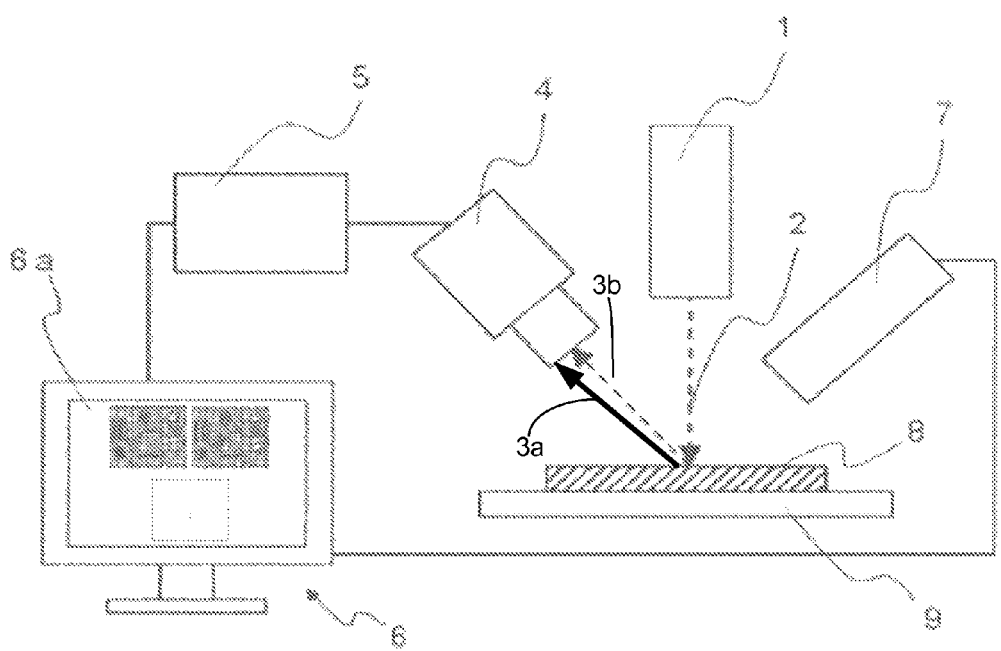
FIG. 2 is an overall structural diagram schematically illustrating an X-ray analyzer according to the present invention.

The X-ray analyzer according to this embodiment is, for example, an energy dispersive fluorescent X-ray analyzer and, as illustrated in FIG. 2, includes: a movable sample stage (moving mechanism) 9 for placing an inspection sample 8 thereon and moving the inspection sample 8; an X-ray tubular bulb (radiation source) 1 for applying a primary X-ray (radiation beam) 2 to an arbitrary irradiation point located on the inspection sample 8; an X-ray detector 4 for detecting a characteristic X-ray 3a and a scattered X-ray 3b which are radiated from the inspection sample 8 and outputting a signal containing energy information on the characteristic X-ray 3a and the scattered X-ray 3b; an optical microscope 7 for obtaining an illumination image of the inspection sample 8, which is illuminated by illumination means (not shown), as image data; an analyzer 5 connected to the X-ray detector 4, for analyzing the signal; and an X-ray mapping processing section 6 connected to the analyzer 5, for performing analysis processing so as to discriminate an X-ray intensity corresponding to a specific element and determining an intensity contrast in which a color or lightness is changed in accordance with the X-ray intensity thus obtained to perform image display at a position corresponding to the irradiation point on a display section 6a.

The X-ray mapping processing section 6 is a computer configured by a CPU and the like and functions as an analysis processing device, and has a function of discriminating the X-ray intensity corresponding to the specific element from an energy spectrum transmitted from the analyzer 5, displaying a two-dimensional image subjected to the X-ray mapping based on the X-ray intensity on the display section 6a, and performing calculation based on the image memory or the image data. In addition, the X-ray mapping processing section 6 is connected to the above-mentioned configuration and has a function of controlling the configuration, and has means for displaying various items of information on the display section 6a in accordance with the control.

Further, the X-ray mapping processing section 6 can be set so that an image of the X-ray intensity and the optical microscope image of the inspection sample 8 obtained by the optical microscope 7 are superimposed on each other to be displayed.

Further, the sample stage 9 is an XYZ stage which is capable of moving horizontally and vertically and adjusting a height thereof by means of a stepping motor (not shown) or the like in a state in which the inspection sample 8 is fixed. The sample stage 9 is controlled by the X-ray mapping processing section 6 so that the irradiation point is caused to shift relative to the inspection sample 8 within a preset mapping area.

Next, with reference to FIG. 2, a method of obtaining a mapping image using the X-ray analyzer according to this embodiment is described. Note that, as the inspection sample 8, an electronic circuit board in which various electronic components such as a resistor are mounted by using a solder material is used, and a concentration distribution of lead (Pb) contained in the solder material or the like is checked through the X-ray mapping.

First, the inspection sample 8 is set on the sample stage 9 and the mapping area to be subjected to the X-ray mapping is input to the X-ray mapping processing section 6 to be set.

Next, the sample stage 9 is driven to move the inspection sample 8 directly below the optical microscope 7, and the mapping area of the inspection sample 8 is imaged by the optical microscope 7, and hence an optical microscope image thereof is transmitted to the X-ray mapping processing section 6 to be stored. Note that, the mapping area is set in advance and then imaged by the optical microscope 7 through the above-mentioned procedure. However, an area in the vicinity of an area of the inspection sample 8, which is expected to be analyzed, may be imaged by the optical microscope 7, and the mapping area may be set based on an optical microscope image thereof.

Next, in order to perform a fluorescent X-ray analysis, the X-ray mapping processing section 6 drives the sample stage 9 to move the inspection sample 8, and places an initial irradiation point within the mapping area at an irradiation point of the primary X-ray 2 emitted from the X-ray tubular bulb 1. The inspection sample 8 is irradiated with the primary X-ray 2 from the X-ray tubular bulb 1 in this state, and hence the characteristic X-ray 3a and the scattered X-ray 3b thus generated are detected by the X-ray detector 4.

The X-ray detector 4 detects the X-ray and then transmits a signal thereof to the analyzer 5, and the analyzer 5 extracts an energy spectrum from the signal and outputs the extracted spectrum to the X-ray mapping processing section 6. The X-ray mapping processing section 6 discriminates an X-ray intensity corresponding to a specific element (in this embodiment, lead) from the energy spectrum transmitted from the analyzer 5, and stores the X-ray intensity as an inspection mapping image information together with coordinate information on the irradiation point.

Further, the irradiation point is caused to be sequentially moved at predetermined distance intervals within the mapping area, and is scanned in matrix, that is, scanned two-dimensionally. Then, the detection described above is repeated for a plurality of irradiation points over the entire mapping area, and hence the information on the inspection mapping image of the respective irradiation points is stored.

Next, the X-ray mapping processing section 6 determines an intensity contrast in which a color or lightness is changed in accordance with the X-ray intensity obtained in the above-mentioned detection by setting one irradiation point as one pixel, and displays the intensity contrast two-dimensionally as an image at a position corresponding to the irradiation point, on the display section 6a.

Figure 1A:
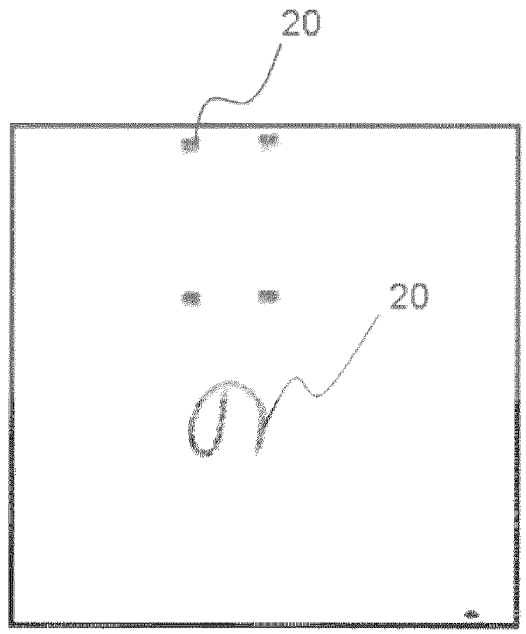
FIG. 1A a concept view illustrating an inspection mapping images in the present invention.
Figure 1B:
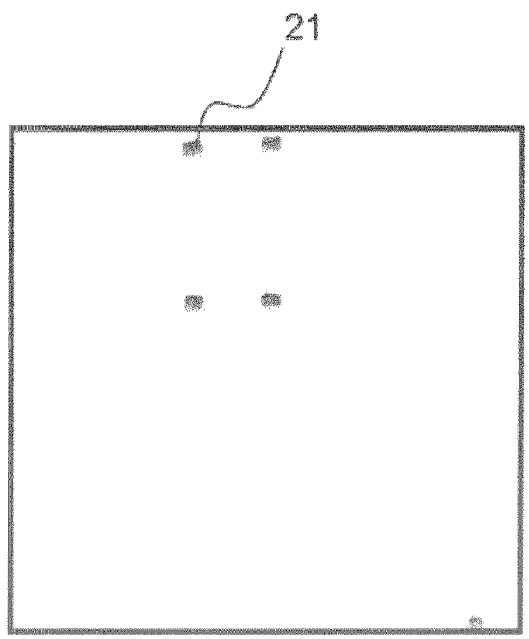
FIG. 1B a concept view illustrating a reference mapping images in the present invention.

For example, an inspection mapping image and a reference mapping image as illustrated in FIGS. 1A and 1B are displayed with an intensity contrast proportional to an X-ray intensity of lead in a mapping area, and hence a difference image of a lead distribution is visually clearly displayed. In this case, when an upper limit value or lower limit value of the intensity contrast is suitably set to display the image, a harmful substance distribution may be determined. When the image is displayed with brightness equal to or higher than expected brightness or when a region which should not originally exist is displayed with high brightness, it is determined to be abnormal.

Figure 1C:
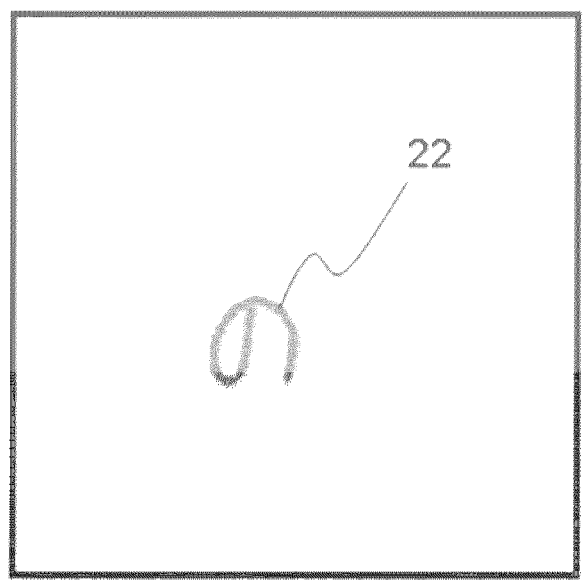
FIG. 1C a concept view illustrating a difference mapping images in the present invention.

A method of obtaining the difference mapping image is described with reference to FIG. 1C. A sample which is determined to be normal and serves as a reference (reference sample) is prepared and then analyzed by the X-ray analyzer according to this embodiment to obtain a mapping image using the method of obtaining a mapping image described above. The obtained mapping image is stored as the reference mapping image in a memory of the X-ray mapping processing section 6. Next, a sample to be inspected (inspection sample) is set in the X-ray analyzer according to this embodiment. As in the case of the reference mapping image, the method of obtaining a mapping image is used to obtain the inspection mapping image and the obtained inspection mapping image is stored in the memory.

Next, the X-ray mapping processing section 6 specifies an element for which a difference is to be obtained, calculates a difference between the inspection mapping image and the reference mapping image at each irradiation point by X-ray intensity subtraction, assigns each obtained result to the same irradiation point as for the inspection mapping image to produce the difference mapping image, and causes the display section 6a to display thereon the produced difference mapping image.

A plurality of elements for which differences are to be obtained may be specified. If necessary, the inspection mapping image, the reference mapping image, and the difference mapping image may be processed by, for example, smoothing or noise removal filtering, and a noise is removed for better visibility.

FIG. 1 illustrates the inspection mapping image (1A), the reference mapping image (1B), and the difference mapping image (1C) of lead, as an example. Element detected regions 20 of the inspection mapping image and element detected regions 21 of the reference mapping image which are displayed with brightness correspond to lead detected portions. Therefore, by obtaining a difference between the inspection mapping image and the reference mapping image, a difference region 22 is produced on the difference mapping image, and hence the difference region which is abnormal is displayed with high visibility. Thus, the inspection mapping image, the reference mapping image, and the difference mapping image are arranged side-by-side and displayed, and hence the abnormal portion may be instantly determined.

When the difference mapping image is to be displayed, a part having a negative difference may be displayed with high brightness corresponding to an absolute value of the difference, or parts having positive and negative differences may be displayed in different colors with changed brightness levels corresponding to absolute values of the differences. Therefore, an element distribution change between the inspection mapping image and the reference mapping image may be visually recognized.

When a plurality of elements are specified, the inspection mapping image, the reference mapping image, and the difference mapping image are arranged side-by-side and displayed for each of the elements, and hence the plurality of elements may be simultaneously inspected.

Figure 3A:
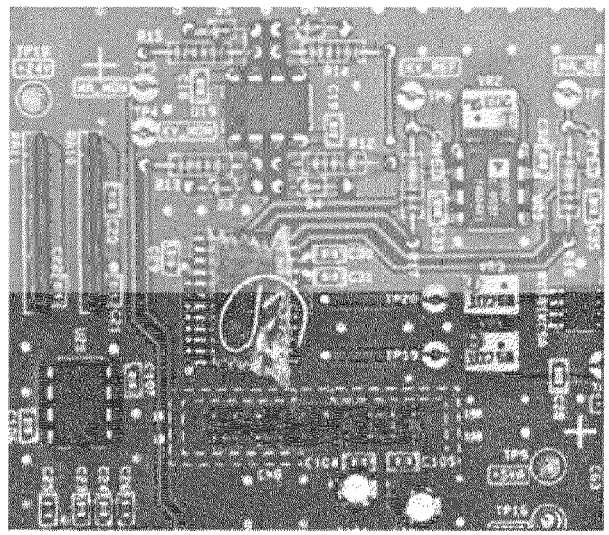
FIG. 3A is a concept view illustrating a optical microscope image of an inspection sample.
Figure 3B:
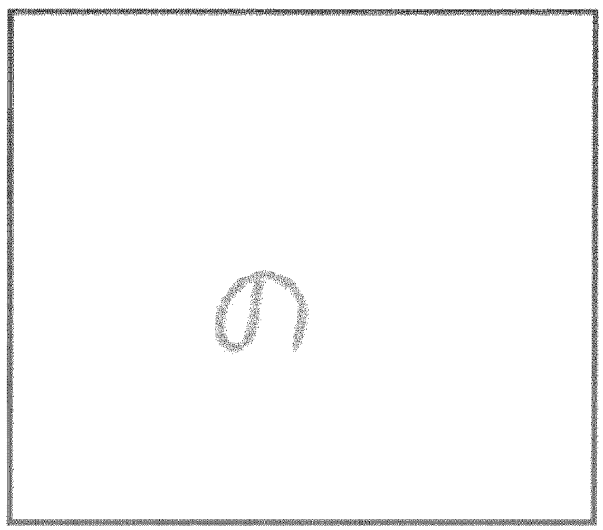
FIG. 3B is a concept view illustrating difference mapping image of an inspection sample.

When the difference mapping image is superimposed on the optical microscope image obtained in the mapping area by the optical microscope 7 of the X-ray analyzer according to this embodiment, the actual state of the abnormal portion may be checked. As illustrated in FIG. 3, an optical microscope image (FIG. 3A) of an inspection sample and a translucently-colored difference mapping image (FIG. 3B) are superimposed on each other to produce a superimposed image (FIG. 3C) of the optical microscope image and the difference mapping image. Therefore, the abnormal portion is exhibited as an abnormal region 23 color-displayed on the optical microscope image, and hence an abnormal position on the sample may be visually determined.

There is a case where the reference mapping image and the inspection mapping image are displaced in position from each other because of, for example, a set state of the sample or a shape difference. In such a case, an optical microscope image for the reference mapping image and an optical microscope image for the inspection mapping image may be used for position correction, rotation correction, and scale correction, to thereby produce the accurate difference mapping image. The corrections may be performed on the reference mapping image and inspection mapping image of a specific element. In this case, a plurality of matching positions are specified for the corrections. Further, the corrections may be automatically performed by using image processing including pattern matching.

With respect to the difference calculation region, an unnecessary calculation part which is known in advance or an inspection which becomes ineffective because of the change of members may be eliminated from a calculation target. Examples of set inspection elimination areas are illustrated in FIG. 4. The inspection elimination areas are set as inspection elimination area-specified part 24 specified by on-screen graphic input using a mouse. For example, a method of separately producing bit map image data in which only inspection elimination areas are filled in and capturing the image data to specify the inspection elimination areas may be employed. When the inspection elimination areas are specified, the sample may be inspected in a suitable inspection area.

In the case of the graphic input using the mouse, graphics may be superimposed on the optical microscope image of the inspection sample, the optical microscope image of the reference sample, the inspection mapping image, and the reference mapping image. When an inspection elimination area is specified using image data, the image data may be captured from the outside.

An image of the inspection elimination area may also be subjected to position correction, rotation correction, and scale correction. The image of the inspection elimination area and the difference mapping image may be superimposed on each other and displayed.

The inspection elimination area may be specified in common to the respective elements or specified for each of the elements. Combinations of the inspection elimination areas and the elements may be used for detailed inspection setting.

In a case where the same type of samples are successively inspected, when the reference mapping images are unified into a single reference, the same reference may be always used for an inspection. The reference mapping image as the reference may be copied and distributed to the same type of X-ray analyzer, and hence a plurality of accurate inspections may be simultaneously and concurrently performed.

Note that, the technical scope of the present invention is not limited to the embodiment described above, and various changes can be made without departing from the gist of the present invention.

For example, the description has been made of the energy dispersive fluorescent X-ray analyzer in the embodiment described above, but the present invention is also applicable to other analysis system as well, such as a wavelength dispersive fluorescent X-ray analyzer or a scanning electron microscope-energy dispersive X-ray spectrometer (SEM-EDS) capable of obtaining a secondary electron image by using an electron beam as a radiation beam to be irradiated.

Further, the description has been made in the embodiment described above that the X-ray mapping processing section 6 can superimpose the image of the X-ray intensity and the optical microscope image of the inspection sample 8 on each other to be displayed. However, the image of the X-ray intensity and the secondary electron image may be superimposed on each other to be displayed in the case where the present invention is adopted in the SEM-EDS.

What is claimed is:

1. An X-ray analyzer, comprising:
   a radiation source for irradiating an irradiation point on an inspection sample with a radiation;
   an X-ray detector for detecting a characteristic X-ray and a scattered X-ray which are radiated from the inspection sample to output, as an X-ray intensity, a signal containing energy information on the characteristic X-ray and the scattered X-ray;
   an analyzer for analyzing the signal;
   a movable sample stage for shifting the irradiation point relative to the inspection sample within a mapping area set in advance;
   an optical microscope system for imaging the mapping area and displaying an image of the mapping area; and
   an X-ray mapping processing section for discriminating an X-ray intensity corresponding to at least one specific element from an analysis result obtained by the analyzer and determining an intensity contrast in which one of a color and lightness is changed in accordance with the X-ray intensity to perform image display at a position corresponding to the irradiation point in the mapping area,
   wherein the X-ray mapping processing section includes:
      reference mapping image storing means for storing a reference mapping image in a measurement area, of a reference sample which is of the same type as the inspection sample and is normal;
      inspection mapping image storing means for storing a test mapping image of the inspection sample in an area corresponding to the inspection area;
      difference calculation means for calculating a difference between an X-ray intensity of the reference mapping image and an X-ray intensity of the inspection mapping image at each radiation point for each pixel, assigning each obtained difference result to the same radiation point and generating a different mapping image; and
      difference mapping image output means for outputting the difference mapping image on a display section.

2. An X-ray analyzer according to claim 1, wherein the difference mapping image output means performs image display with high brightness at either of a position, in which the X-ray intensity of the inspection mapping image is larger than the X-ray intensity of the reference mapping image, or a position, in which the X-ray intensity of the inspection mapping image is smaller than the X-ray intensity of the reference mapping image, after the difference between the X-ray intensity of the reference mapping image and the X-ray intensity of the inspection mapping image is calculated for the each pixel.

3. An X-ray analyzer according to claim 1, wherein the difference mapping image output means performs image display with brightness changed corresponding to a level of the difference between the X-ray intensity of the reference mapping image and the X-ray intensity of the inspection mapping image for the each pixel.

4. An X-ray analyzer according to claim 1, wherein the difference mapping image output means arranges the inspection mapping image, the reference mapping image, and the difference mapping image, to perform image display.

5. An X-ray analyzer according to claim 1, wherein the difference mapping image output means arranges a plurality of the difference mapping images to perform image display when a plurality of the specific elements are provided.

6. An X-ray analyzer according to claim 1, wherein the difference mapping image output means superimposes an optical microscope image of the mapping area which is obtained by the optical microscope system on the difference mapping image to perform image display.

7. An X-ray analyzer according to claim 1, wherein the difference mapping image output means performs one of image correction on the inspection mapping image in comparison with the reference mapping image and image correction on an optical microscope image of the inspection sample in comparison with an optical microscope image of the reference sample which is normal.

8. An X-ray analyzer according to claim 7, wherein the image correction comprises at least one of rotation correction, position correction, and scale correction.

9. An X-ray analyzer according to claim 1, wherein the X-ray mapping processing section further comprises inspection elimination area specifying means for specifying an area, for which difference calculation is unnecessary, as a test elimination area on at least one of an optical microscope image of the inspection sample, an optical microscope image of the reference sample, the inspection mapping image, and the reference mapping image.

10. An X-ray analyzer according to claim 9, wherein the inspection elimination area specifying means specifies the inspection elimination area based on image data captured from an outside source.

11. An X-ray analyzer according to claim 9, wherein the inspection elimination area specifying means sets the inspection elimination area for each element.

12. An X-ray analyzer according to claim 9, wherein: the inspection elimination area specifying means sets zero as a difference value of the specified inspection elimination area; and
the difference mapping image output means displays an image of one of a positive difference value and a negative difference value of an inspection area, relative to the difference value of the specified inspection elimination area, with one of brightness and color to make the image visually recognizable with the one of brightness and color.

13. An X-ray analyzer according to claim 9, wherein the inspection elimination area specified by the inspection elimination area specifying means and the difference mapping image are superimposed on each other and displayed.

14. An X-ray analyzer according to claim 1, wherein the reference mapping image storing means stores image data that has captured from an outside source as the reference mapping image.

15. A mapping method for an X-ray analysis in which:
an irradiation point of a mapping area of an inspection sample which is set in advance is irradiated with a radiation, to thereby detect a characteristic X-ray and a scattered X-ray which are radiated from the inspection sample;
a signal containing energy information on the characteristic X-ray and the scattered X-ray is obtained as an X-ray intensity;
an X-ray intensity corresponding to at least one specific element is discriminated from an X-ray intensity result; and
an intensity contrast in which one of a color and lightness is changed in accordance with the discriminated X-ray intensity is determined, to thereby perform image display at a position corresponding to the irradiation point of the mapping area;
the mapping method for an X-ray analysis comprising:
obtaining a reference mapping image in a measurement area, of a reference sample which is of the same type as the inspection sample and is normal;
obtaining an inspection mapping image of the inspection sample in the same area as the inspection area;
calculating a difference between an X-ray intensity of the reference mapping image and an X-ray intensity of the inspection mapping image at each radiation point for each pixel;
assigning each obtained difference result to the same irradiation point;
generating a difference mapping image; and
outputting the difference mapping image on a display section.

* * * * *